US008889230B2

(12) United States Patent
Flynn et al.

(10) Patent No.: US 8,889,230 B2
(45) Date of Patent: Nov. 18, 2014

(54) SIDE CHAIN FLUOROCHEMICALS WITH CRYSTALLIZABLE SPACER GROUPS

(75) Inventors: Richard M. Flynn, Mahtomedi, MN (US); Michael A. Yandrasits, Hastings, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 271 days.

(21) Appl. No.: 12/377,873

(22) PCT Filed: Aug. 17, 2007

(86) PCT No.: PCT/US2007/076162
§ 371 (c)(1),
(2), (4) Date: Feb. 18, 2009

(87) PCT Pub. No.: WO2008/027736
PCT Pub. Date: Mar. 6, 2008

(65) Prior Publication Data
US 2010/0234521 A1 Sep. 16, 2010

Related U.S. Application Data

(60) Provisional application No. 60/824,187, filed on Aug. 31, 2006.

(51) Int. Cl.
*C08F 18/20* (2006.01)
*C09D 133/16* (2006.01)
*C08F 220/24* (2006.01)
*C07C 67/14* (2006.01)
*C07C 29/62* (2006.01)
*C07C 29/58* (2006.01)
*C07C 69/653* (2006.01)

(52) U.S. Cl.
CPC .............. *C07C 69/653* (2013.01); *C08F 220/24* (2013.01); *C07C 67/14* (2013.01); *C07C 29/62* (2013.01); *C07C 29/58* (2013.01)
USPC ..... 427/427.4; 427/435; 427/439; 427/443.2; 428/421; 526/245; 528/70; 528/401; 560/223

(58) Field of Classification Search
CPC ........ C07C 29/58; C07C 29/62; C07C 67/14; C07C 69/653
USPC ...................... 526/245; 560/223; 528/70, 401
See application file for complete search history.

(56) References Cited

U.S. PATENT DOCUMENTS

| 2,440,800 | A | 5/1948 | Hanford et al. |
|---|---|---|---|
| 2,440,801 | A | 5/1948 | Hanford et al. |
| 2,457,229 | A | 12/1948 | Hanford et al. |
| 2,519,983 | A | 8/1950 | Simons |
| 2,567,011 | A | 9/1951 | Diesslin et al. |
| 2,592,069 | A | 4/1952 | Reid |
| 2,642,416 | A | 6/1953 | Ahlbrecht et al. |
| 2,662,835 | A | 12/1953 | Reid |
| 2,693,458 | A | 11/1954 | Olson |
| 2,727,923 | A | 12/1955 | Husted |
| 2,732,398 | A | 1/1956 | Brice et al. |
| 2,759,019 | A | 8/1956 | Brown et al. |
| 2,764,602 | A | 9/1956 | Ahlbrecht |
| 2,764,603 | A | 9/1956 | Ahlbrecht |
| 2,803,615 | A | 8/1957 | Albrecht et al. |
| 2,803,656 | A | 8/1957 | Ahlbrecht et al. |
| 2,809,990 | A | 10/1957 | Brown et al. |
| 2,846,472 | A | 8/1958 | Van Dyke Tiers |
| 2,875,253 | A | 2/1959 | Barnhart |
| 2,915,554 | A | 12/1959 | Ahlbrecht et al. |
| 3,016,407 | A | 1/1962 | Brace |
| 3,050,555 | A | 8/1962 | Van Dyke Tiers |
| 3,055,953 | A | 9/1962 | Smeltz |
| 3,068,187 | A | 12/1962 | Archibald et al. |
| 3,094,547 | A | 6/1963 | Heine |
| 3,102,103 | A | 8/1963 | Ahlbrecht et al. |
| 3,145,222 | A | 8/1964 | Brace |
| 3,171,861 | A | 3/1965 | Ahlbrecht |
| 3,341,497 | A | 9/1967 | Sherman et al. |
| 3,398,182 | A | 8/1968 | Guenthner et al. |
| 3,514,487 | A | 5/1970 | Anello et al. |
| 3,562,156 | A | 2/1971 | Francen |
| 3,573,332 | A | 3/1971 | Fenton |
| 3,574,791 | A | 4/1971 | Sherman et al. |
| 3,592,866 | A | 7/1971 | Magoon et al. |
| 3,641,171 | A | 2/1972 | Spooncer |

(Continued)

FOREIGN PATENT DOCUMENTS

| EP | 0 526 976 | B1 | 1/1997 |
|---|---|---|---|
| GB | 1102903 | | 2/1968 |

(Continued)

OTHER PUBLICATIONS

Derwent Abstract of SU 389099, 1974.*
*Encyclopedia of Polymer Science and Engineering*, "Telomerization", John Wiley & Sons, Inc., vol. 16, pp. 533-554 (1989).
Boyer et al., "Reverse Iodine Transfer Polymerization (RITP) of Methyl Methacrylate", *Macromolecules*, pp. 4044-4053, vol. 39 (2006).
Boyer et al., "Iodine Transfer Polymerization (ITP) of Vinylidene Fluoride (VDF). Influence of the Defect of VDF Chaining on the Control of ITP", *Macromolecules*, pp. 10353-10362, vol. 38 (2005).
Neal O. Brace, "Radical Addition of Iodoperfluoroalkanes to Vinyl and Allyl Monomers", *Journal of Organic Chemistry* 27, 3033 (Sep. 1962).
International Search Report for International Application No. PCT/US2007/076162.

(Continued)

*Primary Examiner* — Nicole M Buie-Hatcher
(74) *Attorney, Agent, or Firm* — Lucy C. Weiss; H. Sanders Gwin

(57) ABSTRACT

A fluorochemical derived from monomers with a side chain, wherein the side chain includes a perfluoroalkyl group with 1-6 carbon atoms and a hydrocarbon spacer group attached to the perfluoroalkyl group, wherein the spacer group has 15-50 carbon atoms. The perfluoroalkyl group is non-crystallizable at room temperature and the spacer group is crystallizable at room temperature.

13 Claims, 2 Drawing Sheets

(56) References Cited

U.S. PATENT DOCUMENTS

| | | |
|---|---|---|
| 3,787,351 A | 1/1974 | Olson |
| 3,818,074 A | 6/1974 | Ahlbrecht |
| 3,842,019 A | 10/1974 | Kropp |
| 3,896,251 A | 7/1975 | Landucci |
| 3,916,053 A | 10/1975 | Sherman et al. |
| 4,024,178 A | 5/1977 | Landucci |
| 4,043,923 A | 8/1977 | Loudas |
| 4,058,573 A | 11/1977 | Knell |
| 4,147,851 A | 4/1979 | Raynolds |
| 4,264,484 A | 4/1981 | Patel |
| 4,359,096 A | 11/1982 | Berger |
| 4,401,780 A | 8/1983 | Steel |
| 4,484,990 A | 11/1984 | Bultman et al. |
| 4,529,658 A | 7/1985 | Schwartz et al. |
| 4,540,497 A | 9/1985 | Chang et al. |
| 4,564,561 A | 1/1986 | Lore et al. |
| 4,606,737 A | 8/1986 | Stern |
| 4,668,406 A | 5/1987 | Chang |
| 4,716,208 A | 12/1987 | Korzeniowski |
| 5,011,963 A | 4/1991 | Ogawa et al. |
| 5,025,052 A | 6/1991 | Crater et al. |
| 5,207,996 A | 5/1993 | Sierakowski et al. |
| 5,216,097 A | 6/1993 | Allewaert et al. |
| 5,240,574 A | 8/1993 | Fub et al. |
| 5,244,951 A | 9/1993 | Gardiner |
| 5,271,806 A | 12/1993 | Deutsch et al. |
| 5,276,175 A | 1/1994 | Dams et al. |
| 5,380,778 A | 1/1995 | Buckanin |
| 5,431,833 A | 7/1995 | Kondo et al. |
| 5,451,622 A | 9/1995 | Boardman et al. |
| 5,459,212 A | 10/1995 | Krespan et al. |
| 5,468,353 A | 11/1995 | Anich et al. |
| 5,612,431 A | 3/1997 | Waddell et al. |
| 5,641,844 A | 6/1997 | Thompson et al. |
| 5,725,789 A | 3/1998 | Huber et al. |
| 5,744,201 A | 4/1998 | Chang et al. |
| 6,048,952 A | 4/2000 | Behr et al. |
| 6,177,531 B1 * | 1/2001 | Shimada et al. ............... 526/245 |
| 6,326,447 B1 | 12/2001 | Fitzgerald |
| 6,365,769 B1 | 4/2002 | Behr et al. |
| 6,824,882 B2 | 11/2004 | Boardman et al. |
| 2005/0119430 A1 * | 6/2005 | Jong et al. ...................... 526/217 |
| 2010/0234521 A1 | 9/2010 | Flynn et al. |

FOREIGN PATENT DOCUMENTS

| | | |
|---|---|---|
| GB | 1 415 245 | 11/1975 |
| JP | 59-209608 | 11/1984 |
| JP | 60-181093 | 9/1985 |
| JP | 61-020056 | 1/1986 |
| JP | 01-104036 | 4/1989 |
| JP | 07-174480 | 7/1995 |
| JP | 2001-247540 | 9/2001 |
| WO | WO 03/102003 | 12/2003 |

OTHER PUBLICATIONS

Reddy et al., Pair-Wise Interactions by Gas Chromatography IV. Interaction Free Enthalpies of Solutes With Trifluoromethyl-substituted Alkanes, Journal of Chromatography A, (1994), vol. 673, pp. 181-209.

Cloux et al., Pair-Wise Interactions by Gas Chromatography; Part III: Synthesis of Isosteric Stationary Phases for Gas Chromatography, Synthesis, Sep. 1993, No. 9, pp. 909-919.

Napoli et al., "Experimental Surface Activity Measurements of Some Fluorinated Compounds in a Non-Aqueous Medium," *Journal of Fluorine Chemistry*, (1991), vol. 51, No. 1, pp. 103-115.

* cited by examiner

SIDE CHAIN FLUOROCHEMICALS WITH CRYSTALLIZABLE SPACER GROUPS

CROSS REFERENCE TO RELATED APPLICATION

This application claims the benefit of U.S. Provisional Patent Application No. 60/824,187, filed Aug. 31, 2006, the disclosure of which is incorporated by reference herein in its entirety.

TECHNICAL FIELD

This disclosure relates to fluorochemicals (for example, fluorinated polymers and fluorinated urethanes) comprising one or more monomeric units having perfluoroalkyl side chains, to coating compositions comprising the fluorochemicals, and to substrates coated (and methods of coating) therewith. In another aspect, this disclosure relates to methods of making perfluoroalkyl side chain-containing monomers.

BACKGROUND

Fluorinated polymers typically are made up of recurring monomeric units, each monomeric unit including a monomeric backbone portion attached to a perfluoroalkyl side chain. The side chain typically includes a hydrocarbon spacer group that links the side chain to the backbone portion, as well as a terminal hydrophobic perfluoroalkyl tail attached to the spacer group. The stable and inert terminal perfluoroalkyl tail is nonpolar, as well as hydrophobic and oleophobic. Thus, the fluorinated polymers may be mixed with an inert carrier or dissolved in a solvent and applied to a hydrophilic material such as paper, cloth, metals, glass or ceramic to impart to the material water and oil repellency.

The fluorinated polymer can be applied to a substrate surface by, for example, spraying, impregnation, and other methods known in the art of coating. When the fluorinated polymer is applied to the substrate, $CF_3$ tail portions projecting perpendicular to the solid/air interface can create a low surface energy on the substrate, provided that they can be aligned in the proper fashion.

Conventional perfluoroalkyl side chains generally have the formula $C_nF_{2n+1}$—$(CH_2)_m$— where n typically ranges from 6 to 12, and m typically ranges from 1 to 10. It has been postulated that adjusting the number of —$CH_2$— groups in the spacer group, as well as the number of carbon atoms in the $C_nF_{2n+1}$ perfluoroalkyl tail, can result in the alignment of the side chains in the polymers, which in turn results in the formation of crystalline-like regions when the polymer is applied to a substrate. However, in synthesizing conventional fluorinated polymers, the perfluoroalkyl chain length is the only part of the side chain selected to enhance formation of crystalline regions, which is believed to result in close packing by alignment of the side chains.

Preferred commercial products typically include at least about 6 to 12 fluorinated carbons (n≥6) to achieve spontaneous crystallization of the perfluoroalkyl tail portions of the side chains at the application temperature, typically about room temperature. A terminal perfluoroalkyl side chain with n≥6 has been considered necessary to render both hydrophobic and oleophobic the perfluoroalkyl tail of the fluorinated polymeric compound.

SUMMARY

Thus, we recognize that there is a need for alternative side chain materials that can achieve such low surface energies on a wide range of substrates, and we have found that fluorinated polymers and fluorinated urethanes with one or more repeating monomeric units having perfluoroalkyl side chains (herein after also referred to as "fluorinated monomeric units") with the general formula $C_nF_{2n+1}$—$(CH_2)_m$—, wherein n=6-12 and m<10, provide useful repellency properties. Perfluoroalkyl tails with less than 6 carbon atoms combined with methylene spacer groups having less than 10 carbons atoms typically have heretofore exhibited poor water and/or oil repellency.

Briefly, in one aspect, the present disclosure is directed to fluorochemicals (for example, fluorinated polymers and fluorinated urethanes) forming a repellent barrier having low surface energies on a wide range of substrates. The fluorochemicals are derived from monomers that have perfluoroalkyl side chains. The side chains include a perfluoroalkyl group that has 1-6 carbon atoms and is non-crystallizable at room temperature, and a linear hydrocarbon spacer group attached to the perfluoroalkyl group, that has 15-50 carbon atoms and is crystallizable at room temperature.

In one embodiment, the present disclosure is directed to a fluorochemical including at least one recurring monomeric unit having a perfluoroalkyl side chain. The side chain includes a perfluoroalkyl group with 1-6 carbon atoms that is non-crystallizable at about room temperature, and a long chain, linear methylene spacer group with 15-50 carbon atoms that is crystallizable at about room temperature. Suitable monomeric units may vary widely, and include structures derived from fluorinated (meth)acrylates (that is, fluorinated acrylates and/or fluorinated methacrylates) and structures derived from the reaction of a fluorine-containing alcohol with isocyanates, (for example, urethanes).

In another embodiment, this disclosure is directed to a fluorochemical with one or more recurring units derived from organic monomers that have a pendant side chain of the formula: $R_f$-Q-, wherein: $R_f$ is a non-crystallizable perfluoroalkyl group $C_nF_{2n+1}$ with n ranging from 1 to 6 carbon atoms; and Q is a long chain hydrocarbon methylene spacer group —$(CH_2)_m$—, with m ranging from 15 to 50 carbon atoms.

In yet another embodiment, this disclosure is directed to a fluorochemical including a recurring fluorinated structural unit with the formula I:

$$R_f\text{-Q-R} \qquad (I)$$

wherein:

$R_f$ is a non-crystallizable perfluoroalkyl group $C_nF_{2n+1}$ with n ranging from 1-6 carbon atoms, preferably 2-5 carbon atoms, and more preferably 4 carbon atoms;

Q is a long chain hydrocarbon methylene spacer group —$(CH_2)_m$—, with m ranging from 15-50 carbon atoms, preferably 17-40 carbon atoms, more preferably 17-30, and most preferably 17-22 carbon atoms; and R is a group selected from
OC(O)—CR'=$CH_2$,
where R'=H or $CH_3$, and
groups (for example, urethane moieties) that are derived from the reaction of hydroxyl with a multifunctional isocyanate of the general formula:
R"—$(NCO)_x$, where x is 1, 2, 3 or 4 and R" is a suitable aliphatic or aromatic hydrocarbon residue.

In another aspect, this disclosure is directed to a coating composition including the fluorochemicals in a liquid carrier. The coating composition typically is an aqueous solution, which can be a water-based emulsion or include a solvent.

In yet another aspect, this disclosure is directed to a method of applying the fluorochemicals to a substrate to provide improved water and oil repellency.

In another aspect, this disclosure is directed to a substrate having thereon a protective layer including the fluorochemical.

In a further aspect, this disclosure is directed to a method of making a fluorinated monomer comprising: (a) synthesizing an alcohol with the formula $CH_2=CH(CH_2)_pOH$, wherein p ranges from 13 to 48; (b) reacting with the alcohol a perfluoroalkyl iodide having 4-6 carbon atoms to form a perfluoroalkyl iodide substituted alcohol; (c) replacing the iodine atom with hydrogen by reduction and (d) reacting the resulting perfluoroalkyl substituted alcohol to form a fluorinated (meth)acrylate. The fluorinated monomers then can be polymerized to form a fluorinated polymer.

The fluorochemical described herein has a relatively small perfluoroalkyl side chain that is believed to result in low bio-accumulation. One of the advantages of the fluorochemical of the present invention is that it is environmentally friendly, yet still is useful and effective in imparting water and oil repellency. Other advantages include manufacturing and processing efficiency. The small perfluoroalkyl group requires less fluorocarbon starting material by weight, and is relatively easy to process and handle.

DETAILED DESCRIPTION

Figure 1:
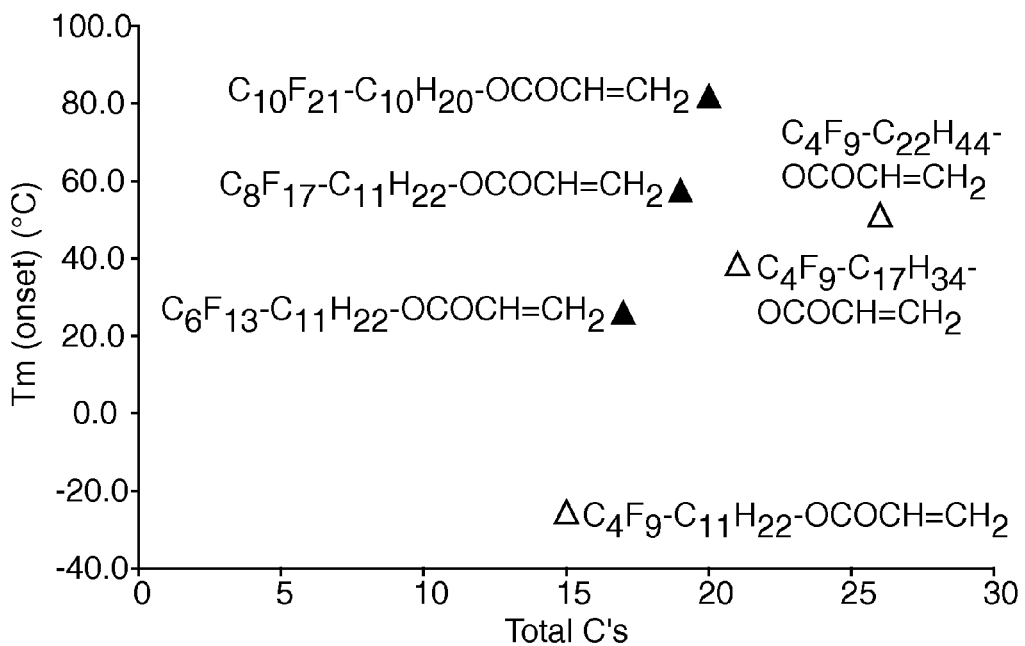
FIG. 1 is a plot of the onset of the melting temperature ($T_m$) vs. total carbon number for $C_nF_{2n+1}$—$(CH_2)_m$-acrylates.

The disclosure relates generally to fluorochemicals (polymers or relatively small molecules that can be termed monomeric or oligomeric) that, when applied to an organic or an inorganic substrate, impart to the substrate useful properties including, for example, soil release, and water and oil repellency. The fluorochemicals are derived from monomers with perfluoroalkyl side chains. The side chains include a perfluoroalkyl group with 1-6 carbon atoms that is non-crystallizable at room temperature and a hydrocarbon spacer group, attached to the perfluoroalkyl group, which has 15-50 carbon atoms and is crystallizable at room temperature. In this application, the term "room temperature" refers to a range of typical application temperatures, preferably about 10° C. to about 40° C., ±1° C., more preferably about 20° C. to about 30° C., ±1° C.

In this application the term "crystallization" refers to the ordering of all or part of the side chain structures such that these chains are aligned. Alignment of polymer chains is an improvement in molecular order. This order can be fully crystalline or partially crystalline including liquid crystalline order and other partially ordered states.

The terms "fluorinated monomeric unit" or "fluorinated monomer" refer to a monomeric unit or monomer having a perfluoroalkyl side chain.

In the fluorinated monomeric units the size and structure of the hydrocarbon spacer group is selected to enhance and control formation of crystalline regions when the fluorochemical is applied to a substrate. These spacer groups have been found to maintain the orientation of the terminal $CF_3$ groups on the perfluoroalkyl tail when the fluorochemical is applied to a substrate, even if the perfluoroalkyl tail has less than 6 carbon atoms. While not wishing to be bound by any theory, based on presently available information, if alignment of the long chain segment of the spacer group can be achieved, then the movement of the side chains may generally be limited and result in improved oil and water repellency on a coated substrate.

The perfluoroalkyl group in the fluorinated monomeric unit side chain preferably has 1-6 carbon atoms, more preferably 2-5 carbon atoms, and most preferably 4 carbon atoms. The hydrocarbon spacer group has 15-50 carbon atoms, preferably 17-40 carbon atoms, more preferably 17-30 carbon atoms, and most preferably 17-22 carbon atoms. The spacer group is typically a linear alkyl group and preferably includes a linear arrangement of methylene (—$CH_2$—) groups.

Preferably, the side chain has the general formula $C_nF_{2n+1}$—$(CH_2)_m$—, wherein n is 1-6, preferably 2-5, and more preferably 4; and wherein m is 15-50, preferably 17-40, more preferably 17-30, and most preferably 17-22. The room temperature crystallization of the methylene group —$(CH_2)_m$— in the side chain typically occurs when m is much greater than 11. Specifically, m is preferably 17 or greater when the number of fluorinated carbons in the pendant side chain is around 4. A crystallizable methylene group —$(CH_2)_m$— of the side chain is possible when m is at least 15 carbons and when the number of fluorinated carbons, n, in the side chain is 6 or smaller. The number of carbon atoms in the methylene spacer group, m, can be adjusted up to 50 carbons to achieve the desired polymeric characteristics.

Generally the melting point of the side chains increases with increasing molecular mass. When the methylene group —$(CH_2)_m$— is too long, the melting point increases, making the fluorochemical harder to handle, which in turn may result in difficulties of applying the fluorochemical and coating the substrates. When m=17-50, the pendant side chain results in good surface alignment and crystallization formation but still the fluorochemical is relatively easy to handle.

Generally, the water and oil repellency imparted to substrates coated with the fluorochemicals of the present invention is due in part to the perfluoroalkyl component. In conventional fluoropolymers, if m is relatively small (less than about 15), when shorter —$(CF_2)_n$—F chains (n is less than 8) are eliminated from the distribution of the side chains, the remaining —$(CF_2)_n$—F groups result in better alignment and crystallization. Short —$(CF_2)_n$—F chains often result in poor water and soil repellency, and poor durability. The present disclosure is directed to side chains with short non-crystallizable fluoroalkyl groups of no more than 6 fluorinated carbons, which is coupled with said long chain and crystallizable methylene segment to provide good durability and water and oil repellency. It is believed that the long chain alkylene segments may facilitate alignment but at the same time allow the perfluoroalkyl tails to remain perpendicular to the surface of the substrate. Substrates treated with the fluorochemicals of the present invention exhibit good water and oil repellency, as well as soil resistance (for example, because the exposed —$CF_3$ end groups maintain an effective barrier against water or oil).

The monomers used to form the fluorochemicals of the present invention may be selected from any organic monomer which, when polymerized, or when reacted with certain reactive functional groups such as hydroxyl, results in a fluorochemical having the above described perfluoroalkyl side chains attached to each repeat unit of its polymeric backbone (to each monomeric backbone portion) or non-polymeric (for example, monomeric or oligomeric) structure. Suitable monomers include fluorinated (meth)acrylates, (meth)acrylamides, vinyl ethers, vinyl esters, styrene derivatives, and urethane precursors (for example, fluorochemical alcohols described herein and mono, di, tri or (poly)isocyanates).

Of the above, the polymeric backbones and non-polymeric structures derived from (meth)acrylates and from urethane precursors (for example, alcohols and isocyanates) are preferred, and from acrylates more preferred.

The monomers described above may be polymerized or copolymerized with other olefinic monomers to improve properties of the final polymeric product without adversely impacting water and soil repellency. Further polymerization or copolymerization may result in better cross-link formation, receptivity or reactivity to particular substrates, film formation, stabilization or improved dispersability in aqueous solvents or emulsions.

Examples of copolymerizable olefinic monomers that can be used (for example, at levels up to about 95 weight percent, based upon the total weight of all monomers used to make the fluorochemical; more preferably, from about 5 to about 70 weight percent) include allyl esters such as allyl acetate and allyl heptanoate; alkyl vinyl ethers or alkyl allyl ethers such as acetyl vinyl ether, dodecylvinyl ether, 2-chloroethylvinyl ether, ethylvinyl ether; unsaturated acids such as acrylic acid, methacrylic acid, alpha-chloro acrylic acid, crotonic acid, maleic acid, fumaric acid, itaconic acid and their anhydrides and their esters such as vinyl, allyl, methyl, butyl, isobutyl, hexyl, heptyl, 2-ethyl-hexyl, cyclohexyl, lauryl, stearyl, isobornyl or alkoxy ethyl acrylates and methacrylates; alpha-beta unsaturated nitriles such as acrylonitrile, methacrylonitrile, 2-chloroacrylonitrile, 2-cyanoethyl acrylate, alkyl cyanoacrylates; alpha, beta-unsaturated carboxylic acid derivatives such as allyl alcohol, allyl glycolate, acrylamide, methacrylamide, n-diisopropyl acrylamide, diacetoneacrylamide, N,N-diethylaminoethylmethacrylate, N-t-butylamino ethyl methacrylate; styrene and its derivatives such as vinyltoluene, alpha-methystyrene, alpha-cyanomethyl styrene; lower olefinic hydrocarbons which can contain halogen such as ethylene, propylene, isobutene, 3-chloro-1-isobutene, butadiene, isoprene, chloro and dichlorobutadiene and 2,5-dimethyl-1,5-hexadiene, and allyl or vinyl halides such as vinyl and vinylidene chloride.

Examples of isocyanates suitable for reaction with the fluorine containing alcohols of this invention include, for example, aromatic diisocyanates such as 4,4'-methylene-diphenylene diisocyanate (MDI) and 2,4-toluene diisocyanate (2,4-TDI); alicyclic diisocyanates such as 3-isocyanatomethyl-3,5,5-trimethyl-cyclohexyl isocyanate (IPDI), 1,4-cyclohexane diisocyanate and 4,4'-cyclohexylmethane diisocyanate; aliphatic diisocyanates such as methylene diisocyanate, 1,6-hexamethylene diisocyanate, 2,2,4-trimethyl-1,6-hexamethylene diisocyanate, and 1,2-ethylene diisocyanate; aliphatic triisocyanates such as 1,3,6-hexamethylenetriisocyanate; aromatic triisocyanates, such as 4,4', 4"-triphenylmethane triisocyanate; polyisocyanates such as polymethylene-polyphenyl-isocyanate (PAPI); isocyanurates, such as the trimer of hexamethylenediisocyanate and the trimer of IPDI and mixtures thereof.

Preferably the amount of comonomers present will not substantially reduce the water repellency or the durability imparted by the side chains, and the fluorochemicals therefore preferably consist essentially of the above-described perfluoroalkyl side chain-containing monomers.

The fluorochemicals according to the invention may contain various crosslinking monomers to provide multi-dimensional curing within the material itself and/or to enhance bonding to the substrate material. Examples of such monomers include N-methylol acrylamide, N(isobutoxymethyl) acrylamide, acrylamide, glycidyl (meth)acrylate, aziridinyl (meth)acrylate, diacetone acrylamide, methylolated diacetone acrylamide, ethylene di(meth)acrylate, hydroxyalkyl (meth)acrylate and the like.

The properties of the fluorochemical can be varied with the use of co-monomers, plasticizers and optionally other additives such as finely divided solids such as carbon black or zinc oxide to affect the handling and delivery systems of the treatment process. For example, the stiffness of a polymer mass can be changed by adjusting a polyfunctional cross-link agent at the time of polymerization. Due to their desirable handling characteristics, acrylate polymers and urethane structures are particularly preferred.

In a preferred embodiment, the fluorochemical includes one or more recurring units derived from organic monomers or structures that have a pendant side chain of the formula: $R_f$-Q-, wherein: $R_f$ is a non-crystallizable perfluoroalkyl group $C_nF_{2n+1}$ with n ranging from 1 to 6 carbon atoms, preferably 2-5 carbon atoms, and more preferably 4 carbon atoms; and Q is a long chain hydrocarbon methylene spacer group —$(CH_2)_m$—, with m ranging from 15-50, preferably 17-40, more preferably 17-30, and most preferably 17-22. In a preferred embodiment, the fluorochemical includes a recurring fluorinated structural unit with the formula I:

$$R_f\text{-Q-R} \qquad (I)$$

wherein:
$R_f$ is a non-crystallizable perfluoroalkyl group $C_nF_{2n+1}$ with n ranging from 1-6 carbon atoms, preferably 2-5 carbon atoms, and more preferably 4 carbon atoms;
Q is a long chain hydrocarbon methylene spacer group —$(CH_2)_m$—, with m ranging from 15-50, preferably 17-40, more preferably 17-30, and most preferably 17-22 carbon atoms; and
R is a group selected from
OC(O)—CR'=$CH_2$,
where R'=H or $CH_3$,
and groups (for example, urethane moieties) that can be derived from the reaction of hydroxyl with an isocyanate of the general formula:
R"—$(NCO)_x$, where x is 1, 2, 3 or 4 and R" is a suitable aliphatic or aromatic hydrocarbon residue.

In another preferred embodiment, a recurring fluorinated monomeric unit is derived from a (meth)acrylate monomer. The fluorinated (meth)acrylate monomers can be prepared by reacting a perfluoroalkyl iodide ($R_fI$) with the double bond of an unsaturated primary alkyl alcohol. This is then followed by a reduction of the iodide and esterification with, for example, a (meth)acrylic acid. The resulting (meth)acrylate monomers with perfluoroalkyl side chains can by polymerized in an appropriate organic solvent, such as hexafluoroxylene, dimethyl formamide, ethyl acetate, other esters, ketones, alcohols, tetrahydrofuran, or any other solvent suitable for free radical polymerizations or by emulsion polymerization in water. The fluorinated polymers can then be isolated for immediate use or for further processing.

The fluorochemicals may be applied on a substrate by spraying, brushing or impregnating the substrate with a coating composition including the fluorochemicals in a liquid carrier. The carrier may be in the form of an aqueous solution or emulsion of the fluorochemical. The solution or emulsion can also be incorporated into a matrix which allows it to migrate to the surface. Following application to the substrate, the coating composition is preferably dried by heating to a temperature above the side chain melt temperature to form an adherent coating on the substrate surface.

The coating composition typically includes 0.05% to 10% by weight of the fluorochemical, preferably 0.01% to 5% by weight, and more preferably about 1% by weight. The solvents selected for use in the coating composition may vary widely, and typically include water and/or any organic solvent that allows crystallization of the spacer group when the coating composition is dried. Some of the exemplary carriers include paraffins, fluorinated or non-fluorinated organic solvents such as $CH_3CFCl_2$, $CF_3CFHCFHC_2F_5$ (4310-mee) and hydrofluoroethers such as HFE-7100 or HFE-7200 available from 3M Company, hexafluoroxylene, dimethyl formamide, alcohols such as ethanol, isopropanol, methoxy propanol and t-butanol, ketones such as isobutyl methyl ketone and methyl ethyl ketone, ethers such as isopropyl ether, methyl t-butyl ether or tetrahydrofuran, esters such ethyl acetate, butyl acetate or methoxypropyl acetate and the like. The coating composition typically includes surfactants, wetting agents, cosolvents, antifoaming agents, dyes, anti-wrinkling agents and other additives known to those skilled in the art.

For example, a coating of about 1% by weight of the fluorochemical material in ethyl acetate may be applied to a fabric substrate and dried in a laboratory oven set to 150° C. for about 5 minutes for proper surface treatment. Alternatively, the substrates can be treated with the fluorochemicals at other concentrations, exposed to different temperatures and time to facilitate the drying process.

The substrate can also be submerged in an aqueous solution or emulsion of the fluorochemicals to obtain a more uniform coating. In an emulsion process, after treating the substrate with the emulsion the treated substrates should preferably be heat treated at or beyond the fluorochemical melting point so that the fluorochemical can melt and re-solidify to form proper alignment on the substrate surface.

Once the coating composition has been applied to a substrate, a protective coating remains that includes the fluorochemical. Ideally a monolayer coating of the fluorochemical is sufficient, but multiple coatings of the fluorochemicals can also be applied using the described or other methods to achieve the desired coating characteristics.

The substrate to which the coating composition is applied can be a natural or synthetic fabric, such as a nonwoven or woven, knit or scrim, but other types of substrate such as yarns, cloths, paper, cellulosic films, leather, glass and ceramic articles and metals can also be effectively treated. The substrate typically will include interstices or passageways or pores that permit flow of fluids and can be used, for example, for garments, furniture or floor coverings, or filter media.

The substrate may also be a natural, synthetic or glass fiber, a polymeric film or a membrane, particularly where the material includes pores that form interstices or pathways.

Due, for example, to the orientation of the fluorochemical molecules, the fluorinated carbon tails provide an inert surface that is both hydrophobic and oleophobic. Thus, drops of water or oil deposited on the surface will form droplets of beads or run off rather than spreading and wetting the surface. Thus, the coating composition is useful as a stainproofing agent, and/or a water, oil, or chemical repellant.

The invention will now be described with respect to certain exemplary embodiments illustrated by the below method steps and the Examples. It should be understood that by specifying certain orders in the present disclosure and chemical reactions (e.g. an order of steps to be performed, certain reducing reagents and catalysts employed, etc.), it is not meant to preclude intermediates between the items specified, other known or alternative steps of performing and/and using other materials to reach a desired reaction scheme.

EXAMPLES

Unless stated otherwise, all chemicals used in following examples were or can be obtained from Sigma-Aldrich, St. Louis, Mo.

Example 1

Synthesis of $CH_2=CH(CH_2)_mOH$ with m=15 and 20

$CH_2=CH(CH_2)_{14}COOH$ and $CH_2=CH(CH_2)_{19}COOH$ were prepared essentially as described in the multi-step syntheses of S. Mirviss, *J. Org. Chem.* 54 1948 (1989).

Under nitrogen atmosphere, a mixture of 21.9 g, 0.082 mol of $CH_2=CH(CH_2)_{14}COOH$ and 250 ml of anhydrous diethyl ether was added drop-wise to a stirred 100 ml solution of 1M lithium aluminum hydride in diethyl ether contained in a dry 500 ml round bottom flask. After a 30-minute addition of the mixture to the flask, the exothermic reaction was allowed to raise the temperature of the reaction mixture to reflux temperature. The reaction was allowed to continue to reflux for four hours and then cooled to 7° C. using an external ice bath.

The cooled reaction mixture was then hydrolyzed slowly with 4 ml water, 4 ml 15% sodium hydroxide, and 12 ml water using a syringe for delivery through a septum port of the 500 ml round bottom flask.

The reaction mixture was then filtered to remove the white solids which form during the neutralization of the hydride. The solvent was removed by rotary evaporation to afford approximately 20 g of $CH_2=CH(CH_2)_{15}OH$. The product was 96% pure as confirmed by gas chromatography/mass spectroscopy (GC/MS) analysis (Finnigan TSQ7000 mass spectrometer, available from Thermo Electron Corporation, Waltham, Mass.) and proton nuclear magnetic resonance (H-NMR) spectrometer (Varian UNITYplus 400 Fourier transform NMR spectrometer, available from Varian NMR Instruments, Palo Alto, Calif.).

In a similar manner, $CH_2=CH(CH_2)_{19}COOH$ (30.4 g, 0.09 mol) dissolved in anhydrous tetrahydrofuran was treated with lithium aluminum hydride (100 ml of a 1M solution in diethyl ether) as described. Using essentially the same procedure as above, approximately 23.2 g of the white solid with 80% purity was obtained as confirmed by GC/MS and H-NMR.

Synthesis of $C_4F_9CH_2CHI(CH_2)_mOH$ with m=15 and 20

$CH_2=CH(CH_2)_{15}OH$ (20 g, 0.079 mol), $C_4F_9I$ (54.5 g, 0.16 mol) and AIBN (azobisisobutyronitrile, 0.5 g) were combined and heated to 70° C. with a brief exothermic reaction, which was allowed to reach 76° C. The reaction mixture was then kept at 70° C. for 16 hours followed by the addition of a second charge of AIBN (0.5 g) and heated for another 4 hours. After the removal of the excess $C_4F_9I$ by rotary evaporation, approximately 44.5 g of product iodohydrin with >85% purity was obtained. The crude iodohydrin product was used in the next step without further purification.

In a similar manner $CH_2=CH(CH_2)_{20}OH$ (23.2 g, 0.072 mol), $C_4F_9I$ (50 g, 0.14 mol) and AIBN (azobisisobutyronitrile, 0.5 g) were reacted to give the corresponding iodohydrin, which was used without further purification in the next step.

Synthesis of $C_4F_9(CH_2)_{17}OH$

Under a nitrogen atmosphere, a mixture of zinc metal (9.7 g, 0.15 mol) and $C_4F_9CH_2CHI(CH_2)_{15}OH$ (44.5 g) was dissolved in 250 ml glacial acetic acid and degassed. After 16 hours at ambient temperature, the reaction mixture was treated with diatomaceous earth (CELITE, available from Celite Corporation, Santa Barbara, Calif.) followed by filtration. The remaining acetic acid solvent was then removed by rotary evaporation. After the solvent evaporated, the residual solids were dissolved in diethyl ether and washed with about 10% aqueous sodium bicarbonate. The combined organic layers were phase separated, filtered and dried over magnesium sulfate. The remaining solvent was further removed by rotary evaporation to furnish 34 g of product.

In addition to the product $C_4F_9(CH_2)_{17}OH$ there were a number of other reaction products including the acetate ester of the product in about an 8:1 alcohol/acetate ratio as well as a significant amount of a dimerized product and some olefins.

The entire reaction mixture was dissolved in methanol and treated with potassium hydroxide (2.0 g, 0.03 mol) in 10 ml water and the solution refluxed for 16 hours. The reaction mixture was poured into water and the tan solids were separated. The solids were further dissolved in diethyl ether to allow complete separation of the remaining water.

The ether solution was washed with brine and dried over magnesium sulfate. The remaining solvent was further removed by rotary evaporation. The residue solids (31 g) were then collected and dissolved in ethanol in a Parr hydrogenation bottle (obtained from Parr Instrument Company, Moline, Ill.). To the bottle 10% palladium on carbon catalyst (0.4 g) was added and the solution was pressurized with hydrogen gas. The Parr hydrogenation apparatus was shaken in order to saturate the olefin products which were formed in the initial reaction. After uptake of hydrogen ceased, the reaction mixture was filtered through a CELITE pad followed by rotary evaporation of the solvent. The final ratio of the saturated product to olefin obtained after the process was approximately 95:5. The product was then recrystallized from hexane to furnish 16.8 g of white solids $C_4F_9(CH_2)_{17}OH$.

Synthesis of $C_4F_9(CH_2)_{17}OAcr$

To a 1 L round bottom flask of 500 ml containing diethyl ether, a mixture of $C_4F_9(CH_2)_{17}OH$ (16.8 g, 0.035 mol) and triethylamine (7.1 g, 0.071 mol) was added. Acryloyl chloride (6.4 g, 0.071 mol) dissolved in 50 ml diethyl ether was then added drop-wise to the 500 ml mixed solution. After three hours the mixture was treated with 300 ml 1N sodium hydroxide, phase separated and further washed with 1N HCl and again with a saturated aqueous sodium chloride solution. The final acrylate product, $C_4F_9(CH_2)_{17}OAcr$ was then collected. The acrylate product was about 91% pure and contained about 1.3% olefin and up to 9% probable dimerized species and a very small amount of remaining alcohol as confirmed by GC/MS, H-1, F-19 and C-13 NMR (Varian UNITYplus 400 Fourier transform NMR spectrometer, available from Varian NMR Instruments, Palo Alto, Calif.).

Example 2

Synthesis of $C_4F_9(CH_2)_{22}OH$

In a similar manner to the synthesis of $C_4F_9(CH_2)_{17}OH$ above, $C_4F_9CH_2CHI(CH_2)_{20}OH$ was treated with zinc in glacial acetic acid to afford a mixture of the reduction product alcohols and acetates as well as their corresponding olefins. The mixture was treated essentially as described above with potassium hydroxide to hydrolyze the acetate esters and finally treated with hydrogen to remove the olefinic impurities and recrystallized from hexane. Approximately 16.8 g of white solids $C_4F_9(CH_2)_{22}OH$ was obtained from this process with 98% purity as confirmed by GC/MS.

Synthesis of $C_4F_9(CH_2)_{22}OAcr$ $C_4F_9(CH_2)_{22}OH$ was then converted to the acrylate in a similar manner as described in the synthesis of $C_4F_9(CH_2)_{17}OAcr$ above. The final acrylate product was about 97% pure as measured by GC/MS. A further analysis of this sample by fast-atom bombardment (FAB) mass spectroscopy indicated that the sample contained roughly 25% of the dimerized product and 75% of the primary acrylate.

Example 3

Polymerization of Fluorochemical Acrylates

A typical procedure for the polymerization of the acrylates of this invention is as follows using $C_4F_9(CH_2)_{17}OAcr$ as a template:

$C_4F_9(CH_2)_{17}OAcr$ (4.0 g) was dissolved in ethyl acetate as solvent. To this solution AIBN (0.04 g) was added and the solution was degassed several times under nitrogen atmosphere using a Firestone valve, available from Sigma-Aldrich, St. Louis, Mo. The solution was then heated to 70° C. for about 18 hours. The homogeneous solution was then poured into aqueous methanol and the resulting polymeric solid precipitated, filtered and washed with water and methanol to dry.

Example 4

Comparative Examples $C_{10}F_{21}(CH_2)_{10}OAcr$ was prepared essentially as described in U.S. Pat. No. 5,641,844.

$C_4F_9(CH_2)_{11}OAcr$ was prepared essentially as described above starting with the AIBN catalyzed addition of $C_4F_9I$ to $CH_2=CH(CH_2)_9OH$. The resulting iodohydrin was reduced with zinc in ethyl alcohol to give the desired $C_4F_9(CH_2)_{11}OH$ and olefinic products in about an 80:20 ratio as follows.

A 1 L round bottom flask containing 575 ml ethanol and zinc metal (19.2 g, 0.29 mol) was heated to 72° C. and the iodohydrin $C_4F_9CH_2CHI(CH_2)_9OH$ (143.7 g, 0.28 mol) was added. After allowing the reaction to proceed to 20% completion for approximately 6 hours, an additional 20 g of zinc metal was added to the mixture. The mixture was then allowed to reflux for 72 hours to reach near completion at 97%. After 72 hours, the reaction mixture was then cooled to room temperature and filtered. The remaining solvent was further "dried off" and removed by rotary evaporation. The residue was distilled under vacuum (165° C./4 mmHg), whereby 55.5 g of a white solid was obtained. GC/MS, H-1, F-19 and C-13 NMR analysis revealed that the collected fraction was a mixture of $C_4F_9(CH_2)_{11}OH$ and a series of olefinic compounds in a ratio of about 80:20.

Other non-alcohol functional materials were present in the product mixture but did not interfere with the acrylation chemistry. Reduction of olefins by hydrogenation will lead not only to reduction of the olefin but also to partial replacement of one of the fluorine atoms and was deemed not to be the method of choice. Therefore the obtained mixture above was used in subsequent reactions without any further reduction of the olefins.

The acrylate monomer was polymerized in ethyl acetate solvent using AIBN initiator as described previously and purified by precipitation with methanol and dissolved in ethyl acetate for testing. Gas Liquid Chromatography (GLC, Hewlett Packard 6890 Series Gas Chromatograph, obtainable from Agilent Technologies, Palo Alto, Calif.) of the ethyl acetate solution of the polymer showed that no residual monomer remained (nor were the non-functional materials noted above present.)

$C_6F_{13}(CH_2)_9OAcr$ was prepared essentially as described above starting with the AIBN catalyzed addition of $C_6F_{13}I$ to $CH_2=CH(CH_2)_9OH$ (which also required two additions of catalyst) and monitoring the reaction by GLC until the starting undecenyl alcohol was consumed. Without further purification the resulting iodohydrin, containing some olefins, was then subjected to catalytic hydrogenation in methanol solvent, which was repeated twice. The first catalytic hydrogenation was achieved by the addition of potassium hydroxide, 2.75 g in 150 ml methanol and the second was achieved without the addition of potassium hydroxide. In both cases the catalyst used in the hydrogenation reaction was 5% Pd on carbon. The resulting alcohol $C_6F_{13}(CH_2)_9OH$ was distilled under reduced pressure (112-114° C./0.15 mmHg) which had a yield of 95% in product purity as measured by GC/MS. The alcohol was then converted to the acrylate using acryloyl chloride and triethylamine as described earlier. The acrylate was then polymerized in ethyl acetate using AIBN as the initiator and purified by precipitation in methanol.

$C_8F_{17}(CH_2)_9OAcr$ was prepared essentially as described above starting with the AIBN catalyzed addition of $C_8F_{17}I$ to $CH_2=CH(CH_2)_9OH$ (which required three additions of catalyst) and monitoring the reaction with GLC until the starting undecenyl alcohol was consumed. The iodoalcohol mixture $C_8F_{17}CH_2CHI(CH_2)_9OH$ was dissolved in 250 ml methanol and 10 g potassium hydroxide. The resulting solution was refluxed for three hours then poured into water. The crude product was extracted with diisopropyl ether and washed once with water. The solvent was then removed by rotary evaporation to yield 84.9 g of the product, which was used as is in the subsequent catalytic hydrogenation.

The product mixture contained about 9.4% of the starting $C_8F_{17}I$ material, which inhibited the hydrogenation reaction completely, as well as 70% of the desired alcohol and 20% of various olefinic products. The reaction mixture was subsequently distilled to completely remove the starting material iodide as a lower boiling cut while the product distilled at 123-128° C./0.1 mmHg. The mixture was then subjected to another catalytic hydrogenation using alcohol solvent (95% ethanol/5% methanol/5% isopropanol) and 0.5 g 10% palladium on carbon catalyst. After filtration of the catalyst and removal of the solvent by rotary evaporation, the desired alcohol $C_8F_{17}(CH_2)_9OH$ was obtained. The alcohol product was 95% pure as confirmed by GC/MS and H-1 and F-19 NMR.

The alcohol was then converted to the corresponding acrylate using acryloyl chloride in tetrahydrofuran with triethylamine as the base essentially as described above except that the reaction mixture was poured into water and extracted into methylene chloride before the wash steps. The acrylate was then polymerized in ethyl acetate using AIBN as the initiator and the polymer precipitated upon cooling after the polymerization was complete. The polymer was completely soluble in benzotrifluoride and was dissolved in this solvent for contact angle measurements.

Example 5

Synthesis of Fluorinated Polymers

Using essentially the same experimental procedures as describe above, two sets of fluoroacrylate polymers were synthesized. The first set was a series of acrylates with 4, 6, and 8 carbons in the fluorochemical chain and an undecenyl methylene spacer connecting to an acrylate backbone. The second set was a series of 17 and 22 methylene spacer groups connecting to a $C_4F_9$-terminal segment at one end of the side chain and to an acrylate backbone at the other.

The $C_4F_9—C_{11}H_{22}—$ material was common to both series. For comparison, materials having longer $R_f$ groups, i.e. $C_8F_{17}—C_{11}H_{22}—$ and $C_{10}F_{21}—C_{11}H_{22}—$, are also shown. Thermal transition data, including melting transition temperatures and dynamic contact angle measurements were made. The results are listed in Tables 1-4 and FIGS. 1-3.

A Differential Scanning Calorimeter (DSC) (Elmer 7 Series Thermal Analysis System) was used to monitor glass melting points and heat of fusion ($\Delta H$) of the polymeric samples. Approximately 10 mg of polymer was placed in an aluminum pan and scanned from −50° C. to 250° C. at 10° C./min. The thermal output during this heating was recorded and reported in Table 1. The melt point was characterized by both the onset and peak temperatures of the melting transition. The heat of fusion was determined to be the area under the melting peak.

TABLE 1

Thermal Data

| Polymer # | $C_nF_{2n+1}—(CH_2)_m—OCOCH=CH_2$ | | Total C | C in FC | C in HC | $T_m$ onset (°C.) | $T_m$ peak (°C.) | $\Delta H$ (J/g) | MW (g/mol) | $\Delta H$ (kJ/mol) | $\Delta S$ (J/Kmol) |
|---|---|---|---|---|---|---|---|---|---|---|---|
| | n | m | | | | | | | | | |
| 1 | 4 | 11 | 15 | 4 | 11 | −25.5 | −14.4 | 8.2 | 444 | 3.6 | 14.7 |
| 2 | 6 | 11 | 17 | 6 | 11 | 26 | 32.2 | 22.4 | 544 | 12.2 | 40.8 |
| 3 | 8 | 11 | 19 | 8 | 11 | 57.6 | 80.6 | 27.5 | 644 | 17.7 | 53.6 |
| 4 | 10 | 11 | 20 | 10 | 10 | 82 | | 24.3 | 730 | 17.7 | 50 |
| 5 | 4 | 17 | 21 | 4 | 17 | 38.6 | 44.5 | 44.4 | 515 | 22.8 | 73.3 |
| 6 | 4 | 22 | 26 | 4 | 22 | 51.3 | 57.8 | 49.9 | 599 | 29.9 | 92.1 |

It was possible that either the fluorocarbon group or hydrocarbon spacer segments of the perfluoroalkyl side chains were responsible for the melt transitions. In an effort to assign the contributions from each segment, the onset of melting for each polymer was plotted as a function of the total number of carbons in the side chain (n+m). The results are shown in FIGS. 1-3.

FIG. 1 shows an approximate 20 degree Celsius increase with each additional fluorinated carbon when the methylene group was held constant at m=11. Conversely, when the number of fluorinated carbons was held constant at n=4, and the number of carbons in the methylene group was allowed to be varied from 11 to 22 carbons, there seemed to be a smaller slope for the melting point profile. On average, there was only about a 7 degree Celsius increase for each additional carbon in the methylene group. The melting point sharply increased when m increased from 11 to 17, and exceeded room temperature but leveled off when m≥17.

Figure 2:
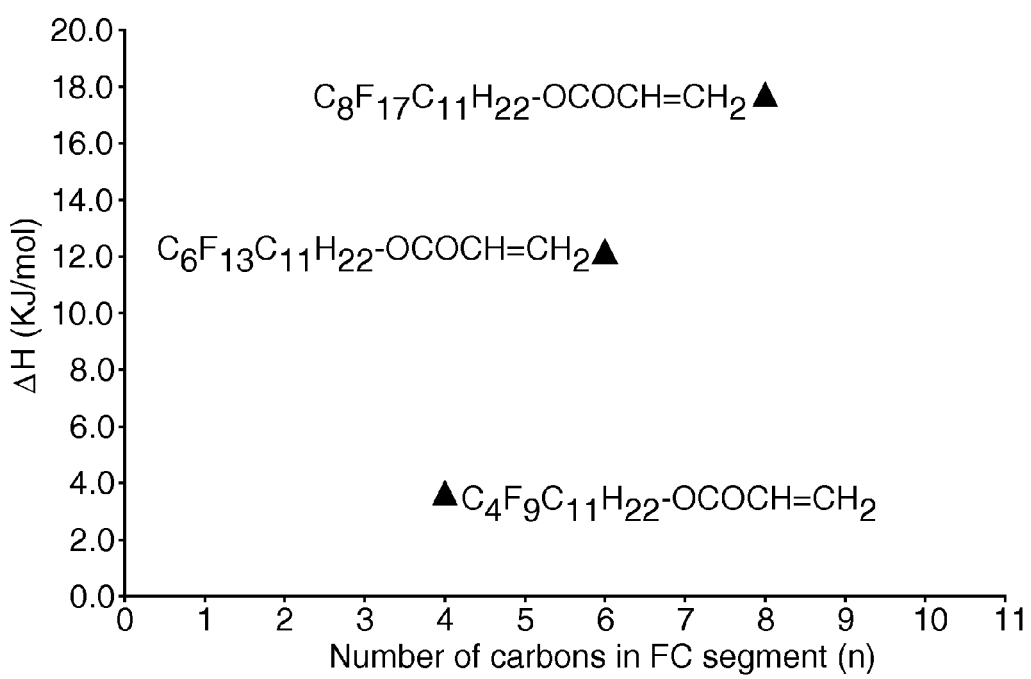
FIG. 2 is a plot of the heat of melting ($\Delta H$) vs. the number of carbons (n) in the perfluoroalkyl segment for $C_nF_{2n+1}$—$C_{11}H_{22}$ acrylates.

Referring to FIG. 2, in which the change in heat of enthalpy, $\Delta H$ (kJ/mol), is presented as a function of the number of fluorinated carbons, n, wherein the number of carbons in the methylene group was held constant at m=11, the heat of enthalpy of the series decreased as the number of fluorinated carbons decreased. The graph shows $\Delta H$ went to zero when n was about 3 fluorinated carbons. This indicates that the methylene group, $—(CH_2)_m—$ was not crystallized when m=11. If the methylene group were organized then one would expect a non-zero value for $\Delta H$ as the number of fluorinated carbons is extrapolated to zero.

Figure 3:
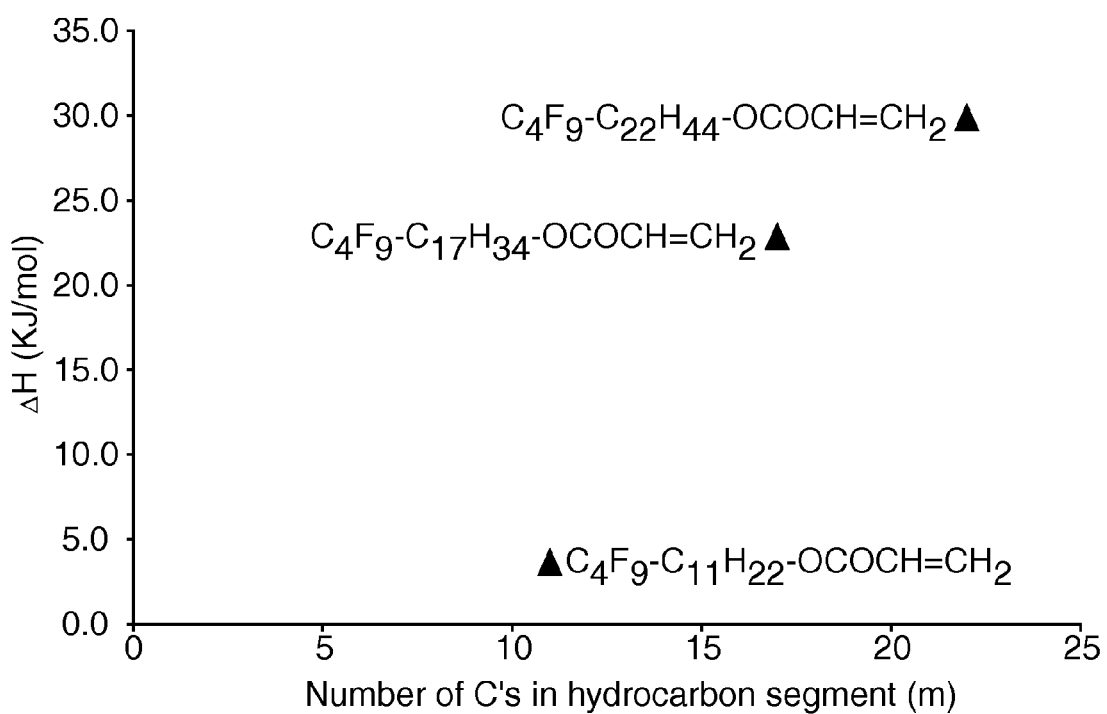
FIG. 3 is a plot of the heat of melting ($\Delta H$) vs. the number of carbons (m) in the hydrocarbon spacer segment for $C_4F_9$—$(CH_2)_m$ acrylates.

Similarly, the change in heat of enthalpy profile for the $C_4F_9$—$(CH_2)_m$-acrylates series, as shown in FIG. 3, showed a decreasing trend as the number of carbons in the methylene group decreased. Again, a ΔH of zero was obtained when the number of carbons in the methylene group was extrapolated to m=10. This result indicates that the fluorocarbon group, $C_nF_{2n+1}$, was not crystallized when n=4.

Generally, this indicates that there was no crystallization of either the methylene group or fluoroalkyl group when the numbers of carbons in the perfluoroalkyl and methylene groups were less than or equal to 4 and 11, respectively.

Example 6

Contact Angle

Contact angles were measured using a Cahn microbalance and the Wilhelmy plate method. A test solution, emulsion, or suspension (typically at about 3% solids in ethyl acetate) was applied to polyester film (available from DuPont) by dip-coating strips of the film. Prior to coating, the film was cleaned with methyl alcohol. Using a small binder clip to hold one end of the nylon film, the strip was immersed in the test solution, and then withdrawn slowly and smoothly from the solution. The coated strip was allowed to air dry in a protected location for a minimum of 30 minutes and then was heat treated for 10 minutes at 150° C.

Advancing and receding contact angles on the coated film were then measured using a CAHN Dynamic Contact Angle Analyzer, Model DCA 322 (a Wilhelmy balance apparatus equipped with a computer for control and data processing, commercially available from ATI, Madison, Wis.). Water and hexadecane (HD) were used as probe liquids. Values for both water and hexadecane are reported in Table 2.

Example 7

Water and Oil Repellency

The water repellency of a substrate was measured using a series of water-isopropyl alcohol test liquids and was expressed in terms of the water repellency rating of the treated substrate. The water repellency rating corresponded to the most penetrating test liquid that did not penetrate or wet the substrate surface after 10 seconds exposure. Substrates which were penetrated by 100% water (0% isopropyl alcohol), the least penetrating test liquid, were given a rating of 0; and substrates resistant to 100% isopropyl alcohol (0% water), the most penetrating test liquid, were given a rating of 10. Other intermediate ratings were calculated by dividing the percent isopropyl alcohol in the test liquid by 10, e.g., a treated substrate resistant to a 70%/30% isopropyl alcohol/water blend, but not to an 80%/20% blend, would be given a rating of 7.

The oil repellency of a substrate was measured by the American Association of Textile Chemists and Colorists (AATCC) Standard Test Method No. 118-1983, which test was based on the resistance of a treated substrate to penetration by oils of varying surface tensions. Treated substrates resistant only to NUJOL mineral oil (the least penetrating of the test oils) were given a rating of 1, whereas treated substrates resistant to heptane (the most penetrating of the test liquids) were given a rating of 8. Other intermediate values were determined by use of other pure oils or mixtures of oils, as shown in the following table of Standard Test Liquids.

TABLE 2

Contact Angles Data

| Polymer # | Polymer | Total C | C in FC | C in HC | Advancing Water (degrees) | Receding Water (degrees) | Advancing HD (degrees) | Receding HD (degrees) |
|---|---|---|---|---|---|---|---|---|
| 1 | $C_4F_9$—$C_{11}H_{22}$—OCOCH=$CH_2$ | 15 | 4 | 11 | 123 | 53 | 81 | 24 |
| 2 | $C_6F_{13}$—$C_{11}H_{22}$—OCOCH=$CH_2$ | 17 | 6 | 11 | 120 | 92 | 76 | 37 |
| 3 | $C_8F_{17}$—$C_{11}H_{22}$—OCOCH=$CH_2$ | 19 | 8 | 11 | 125 | 108 | 83 | 65 |
| 4 | $C_{10}F_{11}$—$C_{11}H_{22}$—OCOCH=$CH_2$ | 20 | 10 | 10 | | | | |
| 5 | $C_4F_9$—$C_{17}H_{34}$—OCOCH=$CH_2$ | 21 | 4 | 17 | 124 | 110 | 80 | 61 |
| 6 | $C_4F_9$—$C_{22}H_{44}$—OCOCH=$CH_2$ | 26 | 4 | 22 | 126 | 112 | 77 | 66 |
| 7 | $C_8F_{17}$—$SO_2(CH_3)N$—$CH_2CH_2$—OCOCH=$CH_2$ | | | | 124 | 111 | 80 | 69 |
| 8 | $C_8F_{17}$—$CH_2CH_2$—OCOCH=$CH_2$ | | | | 125 | 108 | 78 | 73 |

Data in Table 2 show that polymer numbers 5 and 6 formed coatings having low surface energy comparable to known controls, polymer numbers 7 and 8. Data from Table 2 show that the receding water angle substantially increased and leveled off as the total number of carbons in the side chain surpassed 17. For comparison, control polymer numbers 7 and 8, $C_8F_{17}$—$SO_2CH_3N$—$C_2H_4$-OAcr and $C_8F_r$—$C_2H_4$-OAcr had advancing water angles of 124° and 125°, while the examples of the current invention, $C_4F_9$—$C_{17}H_{34}$-OAcr and $C_4F_9$—$C_{22}H_{44}$-OAcr had almost the same advancing water angle values (124° and 126°, respectively). Similarly receding water angle measurements were also essentially the same for both controls and examples.

| Standard Test Liquids | |
|---|---|
| AATCC Oil Repellency Rating Number | Compositions |
| 1 | NUJOL |
| 2 | NUJOL/n-Hexadecane 65/35 |
| 3 | n-Hexadecane |
| 4 | n-Tetradecane |
| 5 | n-Dodecane |
| 6 | n-Decane |
| 7 | n-Octane |
| 8 | n-Heptane |

Water repellency performance of the treated fabric substrates were measured using the American Association of Textile Chemists and Colorists (AATCC) Spray test. Two types of fabric were coated with 1% solution of the $C_4F_9C_{17}H_{34}$— and $C_4F_9C_{22}H_{44}$-materials in ethyl acetate and cured at 120° C. for 5 minutes. The test used a set small quantity of water (250 mL) placed about 15 cm over the fabric substrate, which was set at a 45° angle to the water nozzle. The water was then allowed to gravity feed through a standardized spreader nozzle. A visual rating of how well the water beaded up, based on a scale of 100 points, was then given to the substrate. A rating of 100 was considered as the best when there was no wetting, and a rating of 0 was considered as the worst when there was complete wetting.

TABLE 3

Performance Data

| Polymer # | Polymer | Nylon | | | Polyester | | |
|---|---|---|---|---|---|---|---|
| | | Oil Repellency | Water/IPA Repellency | Spray Rating | Oil Repellency | Water/IPA Repellency | Spray Rating |
| 5 | $C_4F_9$—$C_{17}H_{34}$—$OCOCH=CH_2$ | 3 | 8 | 100 | 4 | 8 | 100 |
| 6 | $C_4F_9$—$C_{22}H_{44}$—$OCOCH=CH_2$ | 3 | 7 | 100 | 3 | 7 | 100 |

Table 3 shows data of performance results of exemplary polymer numbers 5 and 6. Generally, the spray testing showed excellent results. Substrates treated with $C_4F_9$—$C_{17}H_{34}$-OAcry and $C_4F_9$—$C_{22}H_{44}$-OAcry polymers obtained the highest spray rating of 100, which demonstrated the feasibility of this type of side chain polymer for water repellency applications such as textile/rainwear, for example.

Example 8

Bundesmann Rating

The impregnating effect of rain on treated substrates was determined using the Bundesmann Test Method (as described in DIM 53888—German standard test method). In this test, treated substrates were subjected to a simulated rainfall while the back of the substrate was being rubbed. The appearance of the upper exposed surface was checked visually after 1, 5 and 10 minutes and was given a rating from 1 to 5. A rating of 1 indicated complete surface wetting, and a rating of 5 indicated there was no water remaining on the surface.

TABLE 4

Bundesmann Rating With Respect to Time

| Polymer # | Polymer | Nylon | | | Polyester | | |
|---|---|---|---|---|---|---|---|
| | | 1 min | 5 min | 10 min | 1 min | 5 min | 10 min |
| 5 | $C_4F_9$—$C_{17}H_{34}$-Acrylate | 5 | 5 | 5 | 3 | 2 | 2 |
| 6 | $C_4F_9$—$C_{22}H_{44}$-Acrylate | 5 | 5 | 5 | 4 | 3 | 4 |
| 7 | $C_8F_{17}$—$SO_2(CH_3)N$—$CH_2CH_2$-Acrylate | | | | 5 | 5 | 5 |
| 8 | $C_8F_{17}$—$CH_2CH_2$-Acrylate | | | | 5 | 5 | 4 |

Table 4 shows excellent dynamic water repellency for nylon substrates treated with the $C_4F_9C_{17}H_{34}$-Acrylate and $C_4F_9C_{22}H_{44}$-Acrylate polymers, and good dynamic water repellency when these compounds were used on polyester substrates.

Various embodiments of the invention have been described. These and other embodiments are within the scope of the following claims.

What is claimed is:

1. A fluorochemical derived from a monomer composition comprising monomer comprising a side chain, wherein the side chain comprises:
   a perfluoroalkyl group with 4 carbon atoms, wherein the perfluoroalkyl group is non-crystallizable at room temperature; and
   a linear hydrocarbon spacer group attached to the perfluoroalkyl group, wherein the spacer group has 17-22 carbon atoms, is a linear arrangement of methylene groups, and is crystallizable at room temperature;
   wherein said monomer comprising a side chain is selected from a group consisting of (meth)acrylates and urethane precursors and is the only fluorinated monomer present in said monomer composition.

2. The fluorochemical of claim 1, wherein said monomer composition consists essentially of said monomer comprising a side chain.

3. A fluorochemical including at least one recurring monomeric unit having a perfluoroalkyl side chain attached to a monomeric backbone portion, wherein the side chain comprises:
   a perfluoroalkyl group with 4 carbon atoms that is non-crystallizable at room temperature, and
   a long chain, linear methylene spacer group with 17-22 carbon atoms that is crystallizable at about room temperature, and
   wherein the monomeric backbone portion is derived from monomer selected from the group consisting of (meth)acrylates and urethane precursors, and wherein said recurring monomeric unit is the only fluorinated monomeric unit present in said fluorochemical.

4. The fluorochemical of claim 3, wherein the monomeric backbone portion is derived from at least one acrylate monomer.

5. The fluorochemical of claim 3, wherein said fluorochemical consists essentially of said recurring monomeric unit.

6. A fluorochemical with at least one recurring unit derived from monomer that has a side chain of the formula: $R_f$-Q-, wherein: $R_f$ is a non-crystallizable perfluoroalkyl group $C_nF_{2n+1}$ with n being 4 carbon atoms; and Q is a long chain hydrocarbon methylene spacer group —$(CH_2)_m$—, with m ranging from 17 to 22 carbon atoms; wherein said monomer is selected from the group consisting of acrylates and urethane precursors; and wherein said recurring unit is the only fluorinated monomeric unit present in said fluorochemical.

7. The fluorochemical of claim 6, wherein said fluorochemical consists essentially of said recurring unit.

8. A fluorochemical including a recurring monomeric unit with the formula (I):

$$R_f\text{-Q-R} \qquad (I)$$

wherein:
- $R_f$ is a non-crystallizable perfluoroalkyl group $C_nF_{2n+1}$ with n being 4 carbon atoms;
- Q is a long chain hydrocarbon methylene spacer group —$(CH_2)_m$—, with m ranging from 17-22 carbon atoms; and
- R is a group selected from (meth)acrylate groups OC(O)—CR'=CH$_2$, where R'=H or CH$_3$, and groups that are derived from the reaction of hydroxyl with a multifunctional isocyanate of the general formula:

$$R''\text{—(NCO)}_x,$$

where x is 1, 2, 3 or 4 and R'' is an aliphatic or aromatic hydrocarbon residue;

and wherein said recurring monomeric unit is the only fluorinated monomeric unit present in said fluorochemical.

9. The fluorochemical of claim 8, wherein R is a (meth) acrylate group.

10. A coating composition comprising the fluorochemical of claim 8 in a liquid carrier.

11. A substrate having thereon a protective coating, wherein the coating comprises a fluorochemical of claim 8.

12. The fluorochemical of claim 8, wherein said fluorochemical consists essentially of said recurring monomeric unit.

13. A method of treating a substrate comprising applying to the substrate a coating composition comprising a liquid carrier and a fluorochemical including a recurring monomeric unit with the formula (I):

$$R_f\text{-Q-R} \qquad (I)$$

wherein:
- $R_f$ is a non-crystallizable perfluoroalkyl group $C_nF_{2n+1}$ with n being 4 carbon atoms;
- Q is a long chain hydrocarbon methylene spacer group —$(CH_2)_m$—, with m ranging from 17-22 carbon atoms; and
- R is a group selected from (meth)acrylate groups OC(O)—CR'=CH$_2$, where R'=H or CH$_3$, and groups that are derived from the reaction of hydroxyl with a multifunctional isocyanate of the general formula:

$$R''\text{—(NCO)}_x,$$

where x is 1, 2, 3 or 4 and R'' is an aliphatic or aromatic hydrocarbon residue;

and wherein said recurring monomeric unit is the only fluorinated monomeric unit present in said fluorochemical.

* * * * *